(12) United States Patent
Nakamura et al.

(10) Patent No.: US 7,297,224 B2
(45) Date of Patent: Nov. 20, 2007

(54) METHOD OF DEINKING WASTE PAPER USING CELLULASE WITHOUT LOWERING PAPER STRENGTH AND METHOD OF EVALUATING THE SAME

(75) Inventors: Hirofumi Nakamura, Saitama (JP); Hidetoshi Kubota, Saitama (JP); Toshiaki Kono, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 162 days.

(21) Appl. No.: 10/380,420

(22) PCT Filed: Sep. 14, 2001

(86) PCT No.: PCT/JP01/08017

§ 371 (c)(1),
(2), (4) Date: Dec. 16, 2004

(87) PCT Pub. No.: WO02/22943

PCT Pub. Date: Mar. 21, 2002

(65) Prior Publication Data

US 2005/0121156 A1    Jun. 9, 2005

(30) Foreign Application Priority Data

Sep. 14, 2000    (JP) ............................. 2000-279030

(51) Int. Cl.
*D21C 9/00*    (2006.01)

(52) U.S. Cl. ................. 162/5; 162/4; 162/72; 510/174; 435/101; 435/277; 435/278

(58) Field of Classification Search ...................... 162/5
See application file for complete search history.

(56) References Cited

U.S. PATENT DOCUMENTS

| | | | |
|---|---|---|---|
| 4,628,029 A | 12/1986 | Eveleigh et al. | |
| 5,364,501 A | 11/1994 | Baret et al. | |
| 5,582,681 A | 12/1996 | Back et al. | |
| 5,785,809 A * | 7/1998 | Ow et al. | 162/5 |
| 5,912,157 A * | 6/1999 | von der Osten et al. | 435/209 |
| 6,027,610 A | 2/2000 | Back et al. | |
| 6,423,524 B1 * | 7/2002 | Hagen et al. | 435/200 |
| 6,921,655 B1 * | 7/2005 | Nakamura et al. | 435/200 |
| 2002/0142452 A1 * | 10/2002 | Yang et al. | 435/278 |

FOREIGN PATENT DOCUMENTS

| | | |
|---|---|---|
| DE | 19855326 A | 6/2000 |
| JP | 2000-217583 | 8/2000 |
| WO | WO 92/18688 | 10/1992 |
| WO | WO 95/26398 | 10/1995 |
| WO | WO 96/11262 | 4/1996 |
| WO | WO 96/13633 | 5/1996 |
| WO | WO 98/17854 | 4/1998 |
| WO | WO 99/16960 A | 4/1999 |
| WO | WO0024879 A1 * | 5/2000 |

OTHER PUBLICATIONS

L. Pilon, et al, Increasing water retention of mechanical pulp by biological treatments, Jun. 1982, TAPPI, vol. 65, No. 6, pp. 93-96.*

* cited by examiner

*Primary Examiner*—Mark Halpern
(74) *Attorney, Agent, or Firm*—Posz Law Group, PLC; R. Eugene Varndell, Jr.

(57) ABSTRACT

A deinking method using a cellulase which enables the load upon the environment to be reduced; and an evaluation method whereby a cellulase effective in deinking and the effective addition level of the cellulase can be appropriately determined.

By proposing pulp-swelling activity (PSA) that elevates the water-retention value of pulp after pulp is reacted with cellulase, it becomes possible to select an enzyme that is effective in cellulase-deinking treatment without lowering the paper strength and to determine the effective enzyme dosage. Namely, a method of deinking waste paper is provided wherein the selection of an effective cellulase and the optimization of the enzyme dosage with the use of PSA as an indication make it possible to minimize the cellulase addition level and lessen the amount of the deinking agent.

2 Claims, No Drawings

SEQUENCE LISTING

```
<160> NUMBER OF SEQ ID NOS: 6

<210> SEQ ID NO 1
<211> LENGTH: 1017
<212> TYPE: DNA
<213> ORGANISM: Rhizopus oryzae
<220> FEATURE:
<221> NAME/KEY: CDS
<222> LOCATION: (1)..(1017)
<223> OTHER INFORMATION:

<400> SEQUENCE: 1 atg aag ttt att act att gcc tct tcc gct ctc ttg gct ctc gcc ctc    48
Met Lys Phe Ile Thr Ile Ala Ser Ser Ala Leu Leu Ala Leu Ala Leu
1               5                   10                  15 ggt act gaa atg gcc tct gct gct gaa tgt agc aaa ttg tat ggt caa    96
Gly Thr Glu Met Ala Ser Ala Ala Glu Cys Ser Lys Leu Tyr Gly Gln
            20                  25                  30
```

-continued

| | | |
|---|---|---|
| tgt ggt ggt aag aac tgg aat ggc cct act tgt tgt gaa tct gga tcc<br>Cys Gly Gly Lys Asn Trp Asn Gly Pro Thr Cys Cys Glu Ser Gly Ser<br>           35                    40                        45 | 144 |
| acc tgt aaa gta agc aac gat tac tac tct caa tgt ctt ccc tct gga<br>Thr Cys Lys Val Ser Asn Asp Tyr Tyr Ser Gln Cys Leu Pro Ser Gly<br>      50                    55                    60 | 192 |
| agc agt ggc aat aaa tct tct gaa agt gct cac aag aag act acc act<br>Ser Ser Gly Asn Lys Ser Ser Glu Ser Ala His Lys Lys Thr Thr Thr<br>65                   70                    75                    80 | 240 |
| gct gct cac aag aag act act acc gct gct cat aaa aag act acc act<br>Ala Ala His Lys Lys Thr Thr Thr Ala Ala His Lys Lys Thr Thr Thr<br>           85                    90                    95 | 288 |
| gct cct gct aag aag act aca act gtt gcc aaa gct tcc acc cct tct<br>Ala Pro Ala Lys Lys Thr Thr Thr Val Ala Lys Ala Ser Thr Pro Ser<br>          100                 105                110 | 336 |
| aac tct agc tct agc tcc agc ggc aaa tat tcc gct gtc tct ggt ggt<br>Asn Ser Ser Ser Ser Ser Ser Gly Lys Tyr Ser Ala Val Ser Gly Gly<br>          115                 120                125 | 384 |
| gcc tct ggt aac ggt gtc act act cgt tat tgg gat tgc tgt aag gcc<br>Ala Ser Gly Asn Gly Val Thr Thr Arg Tyr Trp Asp Cys Cys Lys Ala<br>130                    135                   140 | 432 |
| tcc tgt agc tgg ccc ggt aag gcc aat gtc agt tct cct gtc aag tcc<br>Ser Cys Ser Trp Pro Gly Lys Ala Asn Val Ser Ser Pro Val Lys Ser<br>145                   150                155                160 | 480 |
| tgt aac aaa gat ggt gtc act gcc ctt agt gac agc aat gcc caa agt<br>Cys Asn Lys Asp Gly Val Thr Ala Leu Ser Asp Ser Asn Ala Gln Ser<br>                 165                170                175 | 528 |
| ggc tgt aac ggt ggt aac agt tac atg tgt aac gac aac caa cct tgg<br>Gly Cys Asn Gly Gly Asn Ser Tyr Met Cys Asn Asp Asn Gln Pro Trp<br>                 180                185                190 | 576 |
| gct gta aac gac aac ctt gcc tat ggt ttc gct gct gct gcc atc agt<br>Ala Val Asn Asp Asn Leu Ala Tyr Gly Phe Ala Ala Ala Ala Ile Ser<br>               195                200                205 | 624 |
| ggt ggt ggt gaa tct cgc tgg tgc tgt tct tgt ttc gaa ctt act ttc<br>Gly Gly Gly Glu Ser Arg Trp Cys Cys Ser Cys Phe Glu Leu Thr Phe<br>210                    215                  220 | 672 |
| act tct acc tct gtt gct ggt aag aag atg gtt gtc caa gtc act aac<br>Thr Ser Thr Ser Val Ala Gly Lys Lys Met Val Val Gln Val Thr Asn<br>225                   230                235                240 | 720 |
| act ggt ggt gat ctt ggc tcc tct act ggt gct cac ttt gac ttg caa<br>Thr Gly Gly Asp Leu Gly Ser Ser Thr Gly Ala His Phe Asp Leu Gln<br>                 245                250                255 | 768 |
| atg ccc ggt ggt ggt gtt ggt att ttc aat ggt tgt tcc agc caa tgg<br>Met Pro Gly Gly Gly Val Gly Ile Phe Asn Gly Cys Ser Ser Gln Trp<br>                 260                265                270 | 816 |
| ggt gct ccc aat gac ggt tgg ggc tca aga tac ggt ggt att tct tct<br>Gly Ala Pro Asn Asp Gly Trp Gly Ser Arg Tyr Gly Gly Ile Ser Ser<br>          275                 280                285 | 864 |
| gca tct gac tgc tct agt ctt cct tcc gca ctc caa gct ggt tgt aaa<br>Ala Ser Asp Cys Ser Ser Leu Pro Ser Ala Leu Gln Ala Gly Cys Lys<br>290                   295                300 | 912 |
| tgg aga ttc aac tgg ttc aag aac gct gat aac cca agc atg act tac<br>Trp Arg Phe Asn Trp Phe Lys Asn Ala Asp Asn Pro Ser Met Thr Tyr<br>305                   310                315                320 | 960 |
| aag gaa gtt acc tgt cct aag gaa atc acc gcc aag aca ggt tgt tca<br>Lys Glu Val Thr Cys Pro Lys Glu Ile Thr Ala Lys Thr Gly Cys Ser<br>                 325                330                335 | 1008 |
| aga aaa taa<br>Arg Lys | 1017 |

<210> SEQ ID NO 2
<211> LENGTH: 338
<212> TYPE: PRT
<213> ORGANISM: Rhizopus oryzae

<400> SEQUENCE: 2

Met Lys Phe Ile Thr Ile Ala Ser Ser Ala Leu Leu Ala Leu Ala Leu
1               5                   10                  15

Gly Thr Glu Met Ala Ser Ala Ala Glu Cys Ser Lys Leu Tyr Gly Gln
            20                  25                  30

Cys Gly Gly Lys Asn Trp Asn Gly Pro Thr Cys Cys Glu Ser Gly Ser
        35                  40                  45

Thr Cys Lys Val Ser Asn Asp Tyr Tyr Ser Gln Cys Leu Pro Ser Gly
    50                  55                  60

Ser Ser Gly Asn Lys Ser Glu Ser Ala His Lys Lys Thr Thr Thr
65                  70                  75                  80

Ala Ala His Lys Lys Thr Thr Thr Ala Ala His Lys Lys Thr Thr Thr
                85                  90                  95

Ala Pro Ala Lys Lys Thr Thr Thr Val Ala Lys Ala Ser Thr Pro Ser
            100                 105                 110

Asn Ser Ser Ser Ser Ser Gly Lys Tyr Ser Ala Val Ser Gly Gly
        115                 120                 125

Ala Ser Gly Asn Gly Val Thr Thr Arg Tyr Trp Asp Cys Cys Lys Ala
    130                 135                 140

Ser Cys Ser Trp Pro Gly Lys Ala Asn Val Ser Ser Pro Val Lys Ser
145                 150                 155                 160

Cys Asn Lys Asp Gly Val Thr Ala Leu Ser Asp Ser Asn Ala Gln Ser
                165                 170                 175

Gly Cys Asn Gly Gly Asn Ser Tyr Met Cys Asn Asp Asn Gln Pro Trp
            180                 185                 190

Ala Val Asn Asp Asn Leu Ala Tyr Gly Phe Ala Ala Ala Ile Ser
        195                 200                 205

Gly Gly Gly Glu Ser Arg Trp Cys Cys Ser Cys Phe Glu Leu Thr Phe
    210                 215                 220

Thr Ser Thr Ser Val Ala Gly Lys Lys Met Val Val Gln Val Thr Asn
225                 230                 235                 240

Thr Gly Gly Asp Leu Gly Ser Ser Thr Gly Ala His Phe Asp Leu Gln
                245                 250                 255

Met Pro Gly Gly Gly Val Gly Ile Phe Asn Gly Cys Ser Ser Gln Trp
            260                 265                 270

Gly Ala Pro Asn Asp Gly Trp Gly Ser Arg Tyr Gly Gly Ile Ser Ser
        275                 280                 285

Ala Ser Asp Cys Ser Ser Leu Pro Ser Ala Leu Gln Ala Gly Cys Lys
    290                 295                 300

Trp Arg Phe Asn Trp Phe Lys Asn Ala Asp Asn Pro Ser Met Thr Tyr
305                 310                 315                 320

Lys Glu Val Thr Cys Pro Lys Glu Ile Thr Ala Lys Thr Gly Cys Ser
                325                 330                 335

Arg Lys

<210> SEQ ID NO 3
<211> LENGTH: 1720
<212> TYPE: DNA
<213> ORGANISM: Trichoderma viride

```
<220> FEATURE:
<221> NAME/KEY: sig_peptide
<222> LOCATION: (171)..(233)
<223> OTHER INFORMATION:
<220> FEATURE:
<221> NAME/KEY: CDS
<222> LOCATION: (171)..(233)
<223> OTHER INFORMATION:
<220> FEATURE:
<221> NAME/KEY: mat_peptide
<222> LOCATION: (234)..()
<223> OTHER INFORMATION:
<220> FEATURE:
<221> NAME/KEY: CDS
<222> LOCATION: (234)..(500)
<223> OTHER INFORMATION:
<220> FEATURE:
<221> NAME/KEY: Intron
<222> LOCATION: (501)..(683)
<223> OTHER INFORMATION:
<220> FEATURE:
<221> NAME/KEY: CDS
<222> LOCATION: (684)..(1607)
<223> OTHER INFORMATION:

<400> SEQUENCE: 3
ggtgtgtcat ttctcctcaa catactgcct ttcaacaact ttcgcctcct ccctggcctg         60
atatcccaat atcagttttt cccaaagtag caagtcatca gtaaatctgc tcatctatca        120
ttaatcagtg cccatagtgt ctgtctgttg attgcctccc gccatacacg atg aac          176
                                                        Met Asn
                                                            -20 agg acc atg gct cca ttg ctg ctt gca gcg tcg ata ctc ttc ggg ggc         224
Arg Thr Met Ala Pro Leu Leu Leu Ala Ala Ser Ile Leu Phe Gly Gly
            -15                 -10                 -5 gct gct gca caa cag act gtc tgg gga cag tgt gga ggt att ggt tgg         272
Ala Ala Ala Gln Gln Thr Val Trp Gly Gln Cys Gly Gly Ile Gly Trp
     -1  1               5                  10 agc gga cct acg agt tgt gct cct gga tca gct tgt tct act ctc aat         320
Ser Gly Pro Thr Ser Cys Ala Pro Gly Ser Ala Cys Ser Thr Leu Asn
         15                  20                  25 cct tat tat gcg caa tgc att ccg ggg gcc act agt atc acc acc tcg         368
Pro Tyr Tyr Ala Gln Cys Ile Pro Gly Ala Thr Ser Ile Thr Thr Ser
 30                  35                  40                  45 acc cga ccc ccc tcg ggt cca acc acc acc aga gcc acc tca acg             416
Thr Arg Pro Pro Ser Gly Pro Thr Thr Thr Arg Ala Thr Ser Thr
                 50                  55                  60 acc tca tct ccg cca ccg acc agc tct gga gtt cga ttt gct ggc gtt         464
Thr Ser Ser Pro Pro Pro Thr Ser Ser Gly Val Arg Phe Ala Gly Val
                 65                  70                  75 aac atc gcg ggc ttt gac ttc gga tgt acc aca gag tatgtcttca             510
Asn Ile Ala Gly Phe Asp Phe Gly Cys Thr Thr Glu
             80                  85 tgttgcatag tgttgctggc tgagtattct gggcggatga tttatagctg tgcgggctgc        570
aaaacaccgc cggtctgcca ctatcaaggc atagttgata ggcggcggtg ttttcttcaa        630
tcccctgatt acactctcaa gaatctagtg gctgatggat gtatgattac agt ggc          686
                                                            Gly
                                                             90 act tgc gtt aca tcg aag gtt tat cct ccg ttg aag aac ttc act ggg         734
Thr Cys Val Thr Ser Lys Val Tyr Pro Pro Leu Lys Asn Phe Thr Gly
             95                 100                 105 gca aac aac tac ccg gac ggt atc ggc cag atg cag cac ttc gtc aac         782
Ala Asn Asn Tyr Pro Asp Gly Ile Gly Gln Met Gln His Phe Val Asn
     110                 115                 120
```

```
gat gat ggg atg act att ttc cgc cta ccc gtc gga tgg cag tac ctc      830
Asp Asp Gly Met Thr Ile Phe Arg Leu Pro Val Gly Trp Gln Tyr Leu
            125                 130                 135 gta aac aac aat ctg ggt gga act ctc gat tcc acc agt atc tcg aag      878
Val Asn Asn Asn Leu Gly Gly Thr Leu Asp Ser Thr Ser Ile Ser Lys
140                 145                 150 tat gat cag ctc gtt cag ggg tgc ctg tct ctc ggt gta tac tgc atc      926
Tyr Asp Gln Leu Val Gln Gly Cys Leu Ser Leu Gly Val Tyr Cys Ile
155                 160                 165                 170 atc gac atc cac aat tat gct cga tgg aac ggt gga atc att ggc cag      974
Ile Asp Ile His Asn Tyr Ala Arg Trp Asn Gly Gly Ile Ile Gly Gln
                175                 180                 185 gga ggc cct aca aat gcc cag ttt acc agt ctt tgg tcg cag ttg gca     1022
Gly Gly Pro Thr Asn Ala Gln Phe Thr Ser Leu Trp Ser Gln Leu Ala
            190                 195                 200 tcg aag tac gcg tct cag tcg agg gtg tgg ttc gga ata atg aat gag     1070
Ser Lys Tyr Ala Ser Gln Ser Arg Val Trp Phe Gly Ile Met Asn Glu
            205                 210                 215 ccc cac gac gtg aac atc aac act tgg gct gcc acg gtt caa gag gtc     1118
Pro His Asp Val Asn Ile Asn Thr Trp Ala Ala Thr Val Gln Glu Val
            220                 225                 230 gtc act gca atc cgc aac gcc ggt gct acg tcg caa tac att tct ctg     1166
Val Thr Ala Ile Arg Asn Ala Gly Ala Thr Ser Gln Tyr Ile Ser Leu
235                 240                 245                 250 cct gga aat gat tat caa tct gcg gca gct ttt att tcc gat ggc agt     1214
Pro Gly Asn Asp Tyr Gln Ser Ala Ala Ala Phe Ile Ser Asp Gly Ser
                255                 260                 265 gca gcc gcc ctg tct cag gta acg aac cct gat gga tca aca acg aat     1262
Ala Ala Ala Leu Ser Gln Val Thr Asn Pro Asp Gly Ser Thr Thr Asn
            270                 275                 280 cta atc ttc gat gtc cac aag tac tta gac tcg gac aac tcc ggt act     1310
Leu Ile Phe Asp Val His Lys Tyr Leu Asp Ser Asp Asn Ser Gly Thr
            285                 290                 295 cac gcc gaa tgc act aca aac aac atc gac ggc gcc ttt gct cct ctc     1358
His Ala Glu Cys Thr Thr Asn Asn Ile Asp Gly Ala Phe Ala Pro Leu
300                 305                 310 gcc act tgg ctt cga cag aac aac cgc cag gct att ctg acg gaa acc     1406
Ala Thr Trp Leu Arg Gln Asn Asn Arg Gln Ala Ile Leu Thr Glu Thr
315                 320                 325                 330 ggc ggt ggc aat gtt cag tcc tgc atc caa gat ttg tgc caa cag atc     1454
Gly Gly Gly Asn Val Gln Ser Cys Ile Gln Asp Leu Cys Gln Gln Ile
                335                 340                 345 cag tac ctc aac cag aac tca gat gtc tat ctt ggc tat gct ggc tgg     1502
Gln Tyr Leu Asn Gln Asn Ser Asp Val Tyr Leu Gly Tyr Ala Gly Trp
            350                 355                 360 ggt gcc ggt tca ttt gat agc act tat att ctg acg gaa acg cct act     1550
Gly Ala Gly Ser Phe Asp Ser Thr Tyr Ile Leu Thr Glu Thr Pro Thr
            365                 370                 375 gga agc ggt aac tcg tgg acg gac aca tcc cta gtt agc tcg tgt ctc     1598
Gly Ser Gly Asn Ser Trp Thr Asp Thr Ser Leu Val Ser Ser Cys Leu
380                 385                 390 gcc agg aag taacaccgag gtcgattgca ggagccttgt caatagcgat            1647
Ala Arg Lys
395 ttcatcttgc tgtacataat tcttactctc tgaagccgct tgttctgggt atgtgtcttg  1707 acaggtttct aga                                                     1720
```

```
<210> SEQ ID NO 4
<211> LENGTH: 418
<212> TYPE: PRT
<213> ORGANISM: Trichoderma viride

<400> SEQUENCE: 4

Met Asn Arg Thr Met Ala Pro Leu Leu Leu Ala Ala Ser Ile Leu Phe
    -20             -15                 -10
Gly Gly Ala Ala Ala Gln Gln Thr Val Trp Gly Gln Cys Gly Gly Ile
-5           -1   1              5                      10
Gly Trp Ser Gly Pro Thr Ser Cys Ala Pro Gly Ser Ala Cys Ser Thr
            15                  20                  25
Leu Asn Pro Tyr Tyr Ala Gln Cys Ile Pro Gly Ala Thr Ser Ile Thr
            30                  35                  40
Thr Ser Thr Arg Pro Pro Ser Gly Pro Thr Thr Thr Arg Ala Thr
        45                  50                  55
Ser Thr Thr Ser Ser Pro Pro Thr Ser Ser Gly Val Arg Phe Ala
60                  65                  70                  75
Gly Val Asn Ile Ala Gly Phe Asp Phe Gly Cys Thr Thr Glu Gly Thr
                80                  85                  90
Cys Val Thr Ser Lys Val Tyr Pro Pro Leu Lys Asn Phe Thr Gly Ala
            95                  100                 105
Asn Asn Tyr Pro Asp Gly Ile Gly Gln Met Gln His Phe Val Asn Asp
            110                 115                 120
Asp Gly Met Thr Ile Phe Arg Leu Pro Val Gly Trp Gln Tyr Leu Val
            125                 130                 135
Asn Asn Asn Leu Gly Gly Thr Leu Asp Ser Thr Ser Ile Ser Lys Tyr
140                 145                 150                 155
Asp Gln Leu Val Gln Gly Cys Leu Ser Leu Gly Val Tyr Cys Ile Ile
                160                 165                 170
Asp Ile His Asn Tyr Ala Arg Trp Asn Gly Gly Ile Ile Gly Gln Gly
            175                 180                 185
Gly Pro Thr Asn Ala Gln Phe Thr Ser Leu Trp Ser Gln Leu Ala Ser
            190                 195                 200
Lys Tyr Ala Ser Gln Ser Arg Val Trp Phe Gly Ile Met Asn Glu Pro
            205                 210                 215
His Asp Val Asn Ile Asn Thr Trp Ala Ala Thr Val Gln Glu Val Val
220                 225                 230                 235
Thr Ala Ile Arg Asn Ala Gly Ala Thr Ser Gln Tyr Ile Ser Leu Pro
            240                 245                 250
Gly Asn Asp Tyr Gln Ser Ala Ala Phe Ile Ser Asp Gly Ser Ala
            255                 260                 265
Ala Ala Leu Ser Gln Val Thr Asn Pro Asp Gly Ser Thr Thr Asn Leu
            270                 275                 280
Ile Phe Asp Val His Lys Tyr Leu Asp Ser Asp Asn Ser Gly Thr His
            285                 290                 295
Ala Glu Cys Thr Thr Asn Asn Ile Asp Gly Ala Phe Ala Pro Leu Ala
300                 305                 310                 315
Thr Trp Leu Arg Gln Asn Asn Arg Gln Ala Ile Leu Thr Glu Thr Gly
            320                 325                 330
Gly Gly Asn Val Gln Ser Cys Ile Gln Asp Leu Cys Gln Gln Ile Gln
            335                 340                 345
Tyr Leu Asn Gln Asn Ser Asp Val Tyr Leu Gly Tyr Ala Gly Trp Gly
            350                 355                 360
```

-continued

```
Ala Gly Ser Phe Asp Ser Thr Tyr Ile Leu Thr Glu Thr Pro Thr Gly
    365                 370                 375

Ser Gly Asn Ser Trp Thr Asp Thr Ser Leu Val Ser Ser Cys Leu Ala
380                 385                 390                 395

Arg Lys

<210> SEQ ID NO 5
<211> LENGTH: 1257
<212> TYPE: DNA
<213> ORGANISM: Humicola insolens
<220> FEATURE:
<221> NAME/KEY: sig_peptide
<222> LOCATION: (118)..(180)
<223> OTHER INFORMATION:
<220> FEATURE:
<221> NAME/KEY: mat_peptide
<222> LOCATION: (181)..()
<223> OTHER INFORMATION:
<220> FEATURE:
<221> NAME/KEY: CDS
<222> LOCATION: (178)..(452)
<223> OTHER INFORMATION:
<220> FEATURE:
<221> NAME/KEY: Intron
<222> LOCATION: (453)..(508)
<223> OTHER INFORMATION:
<220> FEATURE:
<221> NAME/KEY: CDS
<222> LOCATION: (509)..(1088)
<223> OTHER INFORMATION:

<400> SEQUENCE: 5
aatgacgggg caacctcccg cccgggccca actcttgggt ttggttttgac aggccgtctg     60 tctcttgcgt cctcttacta cgcctgcctg gaccctacgt ctcaactccg attcaagatg    120
cgttcctccc ctctcctccg ctccgccgtt gtggccgccg tcccggtgtt ggcccctt     177 gcc gct gat ggc aag tcc acc cgc tac tgg gac tgc tgc aag cct tcg     225
Ala Ala Asp Gly Lys Ser Thr Arg Tyr Trp Asp Cys Cys Lys Pro Ser
 -1   1               5                  10                  15 tgc ggc tgg gcc aag aag gct ccc gtg aac cag cct gtc ttc tcc tgc     273
Cys Gly Trp Ala Lys Lys Ala Pro Val Asn Gln Pro Val Phe Ser Cys
                20                  25                  30 aac gcc aac ttc cag cgt ctc act gac ttc gac gcc aag tcc ggc tgc     321
Asn Ala Asn Phe Gln Arg Leu Thr Asp Phe Asp Ala Lys Ser Gly Cys
            35                  40                  45 gag ccg ggc ggt gtc gcc tac tcg tgc gcc gac cag acc cca tgg gct     369
Glu Pro Gly Gly Val Ala Tyr Ser Cys Ala Asp Gln Thr Pro Trp Ala
        50                  55                  60 gtg aac gac gac ttc gcg ttc ggt ttt gct gcc acc tct att gcc ggc     417
Val Asn Asp Asp Phe Ala Phe Gly Phe Ala Ala Thr Ser Ile Ala Gly
    65                  70                  75 agc aat gag gcg ggc tgg tgc tgc gcc tgc tac ga  gtaagctttg           462
Ser Asn Glu Ala Gly Trp Cys Cys Ala Cys Tyr Glu
80                  85                  90 gtcgcgtgtg taacactgtg caggcatagc actaaccacc tcccag g ctc acc ttc    518
                                                     Leu Thr Phe aca tcc ggt cct gtt gct ggc aag aag atg gtc gtc cag tcc acc agc     566
Thr Ser Gly Pro Val Ala Gly Lys Lys Met Val Val Gln Ser Thr Ser
95                 100                 105                 110 act ggc ggt gat ctt ggc agc aac cac ttc gat ctc aac atc ccc ggc     614
Thr Gly Gly Asp Leu Gly Ser Asn His Phe Asp Leu Asn Ile Pro Gly
                115                 120                 125
```

```
ggc ggc gtc ggc atc ttc gac gga tgc act ccc cag ttc ggc ggt ctg      662
Gly Gly Val Gly Ile Phe Asp Gly Cys Thr Pro Gln Phe Gly Gly Leu
            130                 135                 140 ccc ggc cag cgc tac ggc ggc atc tcg tcc cgc aac gag tgc gat cgg      710
Pro Gly Gln Arg Tyr Gly Gly Ile Ser Ser Arg Asn Glu Cys Asp Arg
        145                 150                 155 ttc ccc gac gcc ctc aag ccc ggc tgc tac tgg cgc ttc gac tgg ttc      758
Phe Pro Asp Ala Leu Lys Pro Gly Cys Tyr Trp Arg Phe Asp Trp Phe
    160                 165                 170 aag aac gcc gac aac ccg agc ttc agc ttc cgt cag gtc caa tgc cca      806
Lys Asn Ala Asp Asn Pro Ser Phe Ser Phe Arg Gln Val Gln Cys Pro
175                 180                 185                 190 gcc gag ctc gtc gct cgc acc gga tgc cgc cgc aac gac gac ggc aac      854
Ala Glu Leu Val Ala Arg Thr Gly Cys Arg Arg Asn Asp Asp Gly Asn
                195                 200                 205 ttc cct gcc gtc cag atc ccc tcc agc agc acc agc tct ccg gtc ggc      902
Phe Pro Ala Val Gln Ile Pro Ser Ser Ser Thr Ser Ser Pro Val Gly
            210                 215                 220 cag cct acc agt acc agc acc acc tcc acc tcc acc acc tcg agc ccg      950
Gln Pro Thr Ser Thr Ser Thr Thr Ser Thr Ser Thr Thr Ser Ser Pro
        225                 230                 235 ccc gtc cag cct acg act ccc agc ggc tgc act gct gag agg tgg gct      998
Pro Val Gln Pro Thr Thr Pro Ser Gly Cys Thr Ala Glu Arg Trp Ala
    240                 245                 250 cag tgc ggc ggc aat ggc tgg agc ggc tgc acc acc tgc gtc gct ggc     1046
Gln Cys Gly Gly Asn Gly Trp Ser Gly Cys Thr Thr Cys Val Ala Gly
255                 260                 265                 270 agc acc tgc acg aag att aat gac tgg tac cat cag tgc ctg             1088
Ser Thr Cys Thr Lys Ile Asn Asp Trp Tyr His Gln Cys Leu
                275                 280 taaacgcagg gcagcctgag aaccttactg gttgcgcaac gaaatgacac tcccaatcac   1148
tgtattagtt cttgtacata atttcgtcat ccctccaggg attgtcacat atatgcaatg   1208
atgaatactg aacacaaacc tggccgcttg aactggccga aggaatgcc              1257

<210> SEQ ID NO 6
<211> LENGTH: 285
<212> TYPE: PRT
<213> ORGANISM: Humicola insolens

<400> SEQUENCE: 6

Ala Ala Asp Gly Lys Ser Thr Arg Tyr Trp Asp Cys Cys Lys Pro Ser
 -1   1               5                  10                  15

Cys Gly Trp Ala Lys Lys Ala Pro Val Asn Gln Pro Val Phe Ser Cys
                 20                  25                  30

Asn Ala Asn Phe Gln Arg Leu Thr Asp Phe Asp Ala Lys Ser Gly Cys
             35                  40                  45

Glu Pro Gly Gly Val Ala Tyr Ser Cys Ala Asp Gln Thr Pro Trp Ala
         50                  55                  60

Val Asn Asp Asp Phe Ala Phe Gly Phe Ala Ala Thr Ser Ile Ala Gly
     65                  70                  75

Ser Asn Glu Ala Gly Trp Cys Cys Ala Cys Tyr Glu Leu Thr Phe Thr
 80                  85                  90                  95

Ser Gly Pro Val Ala Gly Lys Lys Met Val Val Gln Ser Thr Ser Thr
                100                 105                 110

Gly Gly Asp Leu Gly Ser Asn His Phe Asp Leu Asn Ile Pro Gly Gly
            115                 120                 125
```

-continued

```
Gly Val Gly Ile Phe Asp Gly Cys Thr Pro Gln Phe Gly Gly Leu Pro
        130                 135                 140

Gly Gln Arg Tyr Gly Gly Ile Ser Ser Arg Asn Glu Cys Asp Arg Phe
        145                 150                 155

Pro Asp Ala Leu Lys Pro Gly Cys Tyr Trp Arg Phe Asp Trp Phe Lys
160                 165                 170                 175

Asn Ala Asp Asn Pro Ser Phe Ser Phe Arg Gln Val Gln Cys Pro Ala
                180                 185                 190

Glu Leu Val Ala Arg Thr Gly Cys Arg Arg Asn Asp Asp Gly Asn Phe
        195                 200                 205

Pro Ala Val Gln Ile Pro Ser Ser Ser Thr Ser Ser Pro Val Gly Gln
        210                 215                 220

Pro Thr Ser Thr Ser Thr Thr Ser Thr Ser Thr Thr Ser Ser Pro Pro
        225                 230                 235

Val Gln Pro Thr Thr Pro Ser Gly Cys Thr Ala Glu Arg Trp Ala Gln
240                 245                 250                 255

Cys Gly Gly Asn Gly Trp Ser Gly Cys Thr Thr Cys Val Ala Gly Ser
                260                 265                 270

Thr Cys Thr Lys Ile Asn Asp Trp Tyr His Gln Cys Leu
        275                 280
```

METHOD OF DEINKING WASTE PAPER USING CELLULASE WITHOUT LOWERING PAPER STRENGTH AND METHOD OF EVALUATING THE SAME

TECHNICAL FIELD

The present invention relates to a method of deinking waste paper that lessens the load on the environment. The invention further relates to a method that evaluates cellulase that is effective in deinking whereby the paper strength (intensity) is not reduced and a usage amount of deinking agents is lowered, and an effective dosage of the cellulase.

BACKGROUND ART

Deforestation is cited as a cause of global warming and the reduction of carbon-dioxide emissions is the focus of attention as a global environmental problem. Forest resources are utilized in contemporary industries in the forms of wood, pulp, and paper. Various methods are being studied to reduce the amount of deforestation in order to prevent global warming. In the field of paper, efforts are being made worldwide to increase the rate of waste paper recycling.

Waste paper deinking is largely established as a method of waste paper recycling. In current methods, alkalis such as sodium hydroxide and sodium silicate, oxidative bleaching agents such as hydrogen peroxide, chelating agents, and agents such as surfactants are added to the waste paper to accelerate the release of ink from the pulp fiber. Thereafter, a washing technique and/or flotation technique is used to carry out deinking to separate the pulp and ink.

However, due to the variety of raw materials used in waste paper and the variety of printing techniques, deinking by the conventional deinking techniques is becoming problematic. Further, in order to solve problems concerning adhesion of foreign matter (stickies), fiber damage, effluent load and the like, neutral deinking is attracting attention as a deinking method that is kinder to the environment. In order to carry out neutral deinking more effectively, enzymatic treatments utilizing cellulase and the like are being studied.

A number of proposals have been put forth concerning deinking methods for waste paper using cellulase derived from fungi or bacteria. Kao Corp. proposes a deinking agent containing cellulase in JP Patent Publication (Unexamined Application) No. 59-9299, however there is no disclosure therein regarding the putative lowering of paper strength due to the action of the cellulase. In JP Patent Publication (Examined Application) No. 3-57235, Honshu Paper Co., Ltd. proposes a deinking technique for waste paper in which enzymatic treatment using alkali-resistant cellulase is performed at the same time as treatment with an alkaline deinking agent or after treatment with the deinking agent. In Japanese Patent No. 2805313, Oji Paper Co., Ltd. discloses a deinking technique in which treatment is conducted with a deinking agent after enzymatic treatment that contains cellulase. Further, in Japanese Patent No. 3042718, Novo Nordisk A/S attempts to find an enzyme component that can perform effective deinking by producing monocomponent cellulase. However, none of the above methods succeeded in providing an effective means for selecting an enzyme that realizes, at a low cost, a deinking effect that reduces the amount of the chemical agents that constitute an environmental burden or lower the strength (intensity) of waste paper in deinking.

Although various studies are being conducted, the rate of diffusion of enzymatic deinking is extremely low. Up to now, studies have been conducted on the application of cellulases to areas such as elimination of vessel pick, improvement of paper machine runnability and drainage, and deinking of waste paper. However, because of the high cost of cellulases and the fact that the action and effects of cellulases is not clear, the current situation is that cellulase has not been offered for practical use in areas other than elimination of vessel pick. Furthermore, because cellulase is an enzyme that degrades cellulose fiber, it has been pointed out that a decrease in the yield and the strength (intensity) of waste paper pulp after deinking is prone to occur.

Meanwhile, in deinking of waste paper, because the objects of effective deinking involve detachment and saponification of printing ink and pulp swelling, alkaline chemical agents and the like are used that amount to as much as several percent of the dry pulp weight. Further, as pulp is normally treated by being suspended in water of a volume that is equivalent to several dozen times the weight of the dry pulp, a vast amount of alkaline effluent is generated. Thus, because chemical agents are used in the treatment to neutralize the effluent, the recovery treatment is one that involves a heavy environmental burden. There is a need for development of an environmentally friendly deinking method that improves the current deinking technology that creates a heavy environmental burden.

Waste paper recycling is technology that indirectly protects forest resources and contributes to conservation of the global environment. It is anticipated that by further improvements such as reducing the environmental burden caused by waste effluent and decreasing the usage amount of chemical agents, the environmental adaptability of waste paper recycling will be enhanced. Thus, it was expected that enzymatic deinking would be applied as a technique to effectively remove ink at a neutral pH. However, its application has been postponed due to problems concerning decreases in the strength (intensity) of waste paper pulp and the cost of enzymes. Accordingly, the object of the present invention is to provide a cellulase deinking method for waste paper without lowering paper strength, that is implemented using an economically feasible enzyme amount that reduces the amount of deinking agents.

DISCLOSURE OF THE INVENTION

As described above, in waste paper deinking using cellulase, it is desirable that the deinking effect be obtained using a cost-effective amount of enzyme without lowering the paper strength (intensity). Therefore, we tested a fraction of each cellulase component of cellulases derived from fungi, and evaluated the activity of the obtained enzyme components towards pulp, the waste paper deinking action, and the intensity characteristics of the enzyme-treated waste paper.

Surprisingly, we found that by allowing an extremely small level of cellulase components comprising a marked amount of endoglucanase to act on pulp, the conventionally known action of cellulase of degrading cellulose to yield cellulose degradation products such as glucose hardly occurred, and the degree of swelling, which is indicated by the water retention value of the pulp, increased. Specifically, we found that the cellulose fiber constituting the pulp was hydrated to cause the pulp to swell. Conventionally, pulp swelling is an effect that has been found in sodium hydroxide and liquid ammonia, which are alkaline chemical agents, however this phenomenon had not been found with regard to cellulase.

As a result of further concentrated studies, we found that, with regard to pulp swelling and waste paper deinking effects produced by cellulase, a favorable correlation exists in the kinds of cellulase effective in waste paper deinking and the kinds of cellulase having a swelling action. As a result, we found that, surprisingly, fungi-derived endoglucanase expresses waste paper deinking activity in a dosage level that is lower than the enzyme dosage used in treatment reported up to now, and also that the intensity of waste paper that underwent enzymatic deinking compared favorably to the intensity of the waste paper prior to the enzymatic treatment. Further, when we compared deinking activity exerted by endoglucanase with that of sodium hydroxide, sodium silicate, and hydrogen peroxide, which are deinking agents that are currently in widespread use, we found that cellulase reduces the usage amount of these chemicals, or exhibits an effect that adequately substitutes for these chemicals. Thus we succeeded in completing the present invention.

Namely, by evaluating pulp-swelling activity (PSA) that is determined by measuring an increase in the water retention value of pulp according to the present invention, it is possible to determine an effective enzyme and an effective enzyme usage level for a target waste paper deinking application.

The present invention relates to a method of deinking waste paper characterized by the use of cellulase that exhibits pulp-swelling activity (PSA). The present invention further relates to: a method characterized by being conducted with cellulase of a dosage level wherein pulp-swelling activity (PSA) is 25 units (25 U) or more; a method characterized by being conducted with cellulase of a dosage level wherein pulp-swelling activity (PSA) exhibits a maximum value; a method wherein the cellulase is endoglucanase; and the above method wherein endoglucanase is SCE3 derived from *Trichoderma* genus, NCE4 derived from *Humicola* genus, or RCEI derived from *Rhizopus* genus.

The present invention also relates to an evaluation method for obtaining a cellulase enzyme and an enzyme dosage that are effective in deinking of waste paper without lowering the paper strength. The present invention further relates to: an evaluation method characterized by measuring the degree of swelling of pulp after reacting cellulase with pulp; an evaluation method characterized by measuring a change in the water retention value (WRV) of pulp after reacting pulp with cellulase for 60 min at the optimal pH and optimal temperature of the enzyme used at a pulp consistency of 1% (w/v); and to an evaluation method characterized by determining pulp-swelling activity (PSA), wherein cellulase activity that increases the water retention value (WRV) of pulp by 1% is taken as 10 units (10 U) after reacting cellulase for 60 min under conditions of a pulp consistency of 1% (w/v), optimal pH, and optimal temperature, employing 0.5 g of oven-dried pulp as a substrate.

Cellulase used in the present invention is characterized by containing endoglucanase. More specifically, cellulase containing monocomponent endoglucanase or specific endoglucanase components in a large amount or the like can be used, but a method of manufacturing the enzyme preparation is not limited. Further, the origin of endoglucanase contained in the cellulase may be any organism that produces endoglucanase, such as fungi (*Trichoderma* genus, for example *T. reesei* or *T. viride*; *Humicola* genus, for example *H. insolens*; *Acremonium* genus, for example *A. cellulolyticus*; *Rhizopus* genus, for example *R. oryzae*; *Mucor* genus, for example *M. circinelloides*; *Phycomyces* genus, for example *P. nitens*; and the like) or bacteria (*Bacillus* genus, *Pseudomonas* genus, *Clostridium* genus, and the like) or the like. Further, an enzyme derived from a transformant in which a gene of the above endoglucanases is introduced can be used, and the origin is not limited by the present description.

Cellulase is an enzyme that degrades a water-insoluble cellulose substrate by the synergistic action of a number of kinds of enzyme, and β-glucosidase, endoglucanase, and cellobiohydrolase are known components thereof. For example, known components of endoglucanase derived from *Trichoderma* genus include EG I to EG IV, and known components of endoglucanase derived from *Humicola* genus include EG I to EG V, and all of these can be utilized in the method of the present invention. Further, each component of cellulase may be classified into a sugar hydrolase family as proposed by Hennrissat et al. In recent years, it has become known that families in which endoglucanase (EC.3.2.1.4) is present include 5, 6, 7, 8, 9, 12, 44, 45, 48, 51, 61, 74 and the like. For example, it is known that endoglucanase II derived from *Trichoderma viride* is classified into family 5, and endoglucanase V derived from *Humicola insolens* is classified into family 45.

Commercially available cellulase is mainly produced as a mixture of the above three components by a microorganism such as bacteria or fungi. By devising the conventional culture conditions it has been possible to somewhat alter the composition ratio of enzyme components, but imparting a major alteration has proved difficult. However, because the selection and expression of a specified gene has become possible as a result of progress in genetic engineering techniques in recent years, the possibility has increased of being able to isolate and identify a specific cellulase component effective in treatment of paper pulp and, furthermore, to manufacture a highly expressing clone to create a novel enzyme that offers excellent cost efficiency.

The present inventors already provide cellulase derived from *Trichoderma* genus, cellulase derived from *Humicola* genus, cellulase derived from *Rhizopus* genus, and the like, as the above kind of cellulase derived from fungi. Similar cellulases are also provided by Genencor mt. Inc., Novo Nordisk A/S, logen Corp., and the like. Meanwhile, KAO Corp. provides *Bacillus* genus cellulase as cellulase derived from bacteria. In the present invention, it is also possible to use these cellulases. Preferable examples to be used herein include SCE3 (SEQ ID NO:3 and SEQ ID NO:4), which is endoglucanase derived from *Trichoderma* genus, NCE4 (SEQ ID NO:5 and SEQ ID NO:6), which is endoglucanase derived from *Humicola* genus, RCE1 (SEQ ID NO:1 and SEQ ID NO:2), which is endoglucanase derived from *Rhizopus* genus, and the like, which are already provided by the present inventors.

In the present invention, as endoglucanase we selected SCE3 disclosed in WO 98/54332 as cellulase derived from *Trichoderma* genus and NCE4 disclosed in WO 98/03640 as cellulase derived from *Humicola* genus, and conducted a comparison of the deinking activity by means of the following experiments.

Method for Determining Pulp-swelling Activity (PSA)

The pulp-swelling activity (PSA) as proposed by the present invention was determined in the following manner. 0.5 g of oven-dried pulp that was disintegrated for 20 min by a standard disintegrator as described in JIS (Japanese Industrial Standard) P-8209 was suspended in a buffer solution having the optimal pH for the enzyme to be used in evaluation to bring the pulp consistency to 1% (w/v), and the enzyme was then added thereto and reacted at the optimal temperature for 60 min. To measure the degree of swelling of the pulp after reaction, the water retention value (WRV), which is one indicator of the degree of swelling, was measured according to the water retention value (WRV) measurement method for pulp described on p. 73 of "KAMI PARUPU NO SHIKENHOU (A method for testing paper pulp)" (edited and published by The Japan Technical Association of the Pulp and Paper Industry, 1995). The degree of swelling (water retention value) was also measured for untreated pulp in the same way. The water retention value of the pulp treated with enzyme was compared with the water retention value of the untreated pulp, and enzyme activity that increased the water retention value by 1% was taken as 10 units (10 U), and the unit was defined as pulp-swelling activity (PSA).

The pulp-swelling activity (PSA) is not necessarily proportional to the added level of enzyme, however, when the level of added enzyme is too small PSA decreases as the pulp does not swell, and when the level of added enzyme is too large PSA decreases because the cellulose fibers of the pulp are excessively cut and water cannot be contained among the fibers. Therefore, PSA exhibits a peak (maximum value) at an enzyme dosage within a certain range.

Because the deinking effect is enhanced as pulp-swelling activity (PSA) increases, a preferable enzyme for carrying out the present invention is an enzyme that exhibits a higher numerical value for PSA even when the added level of the enzyme is small. Specifically, a preferable enzyme is one exhibiting a pulp-swelling activity (PSA) value of 25 units (25 U) or more per 0.5 g of oven-dried pulp. Further, when the added amount of enzyme used exhibits a pulp-swelling activity (PSA) value of 25 units (25 U) or more, as previously described, it is preferable that the PSA value is in the vicinity of its maximum, and the range thereof suitably changes according to the enzyme used.

In the present invention, the optimal pH and optimal temperature of an enzyme can be determined by the following procedure. Buffer solutions used herein in determining the optimal pH are as follows: for pH 4 to 5.5, a 50 mM acetate buffer; for pH 6 to 8, a 50 mM phosphate buffer; and for pH 9, a 50 mM glycine-sodium hydroxide buffer.

0.5 ml of solution containing enzyme is added to 0.5 ml of buffer solution containing 2% of CMC (carboxymethylcellulose, manufactured by Tokyo Kasei Kogyo Co., Ltd.) dissolved therein, and the mixture is then incubated at 30 to 70° C. for 30 min. Subsequently, the concentration of reducing sugar produced in the obtained reaction solution is determined by a 3,5-dinitrosalicylic acid method (DNS method). More specifically, 3.0 ml of DNS reagent is added to 1.0 ml of reaction solution 30 min. after reaction, the mixture is incubated for 5 min in a boiling water bath, diluted with 8.0 ml of distilled water, and the absorbancy at 540 nm is then determined. A calibration curve is then created using glucose solution diluted in a stepwise manner, and the amount of reducing sugar produced in the enzyme reaction solution is determined using glucose conversion. Activity is calculated by taking as 1 unit an enzyme level that produces reducing sugar corresponding to 1 μmol of glucose in 1 min. The DNS reagent can be prepared in accordance with descriptions in the literature (for example, "SEIBUTSU KAGAKU JIKKENHOU 1—KANGENTOU NO TEIRYOUHOU (Biochemical experimental method 1—Quantitative method of reducing sugar)" p. 19-20, 1981, Fukui Sakuzou, GAKKAI SHUPPAN CENTER).

Deinking Activity of Cellulase

The deinking activity of cellulase was determined as described below when using waste newspaper cut into 3 cm-square pieces as the raw material waste paper. Waste paper pulp was obtained by disintegrating 24 g of oven-dried raw material waste paper at 50° C. for 20 min using a standard disintegrator as described in JIS P-8209. Cellulase was added to the waste paper pulp for which the pH was adjusted by buffer solution or sulfuric acid, and enzyme reaction was conducted for 1 hour at 50° C. After the reaction, distilled water at 50° C. was added to the waste paper pulp to bring to 4.5 L, the mixture was provided to an experimental flotator (FW model flotation test apparatus, manufactured by KYOUSIN SANGYOU CO., LTD.), a deinking agent (Lipotol LH-350, manufactured by NIKKA Chemical Co., Ltd.) of 0.1 to 0.5% (w/v) of the oven-dried pulp was added thereto, and flotation was conducted for 10 min. The pulp was then recovered, washed with distilled water and dehydrated, diluted with distilled water to bring to a pulp consistency of 0.15% (w/v), and made into paper using a handsheets machine according to a method described in JIS P-8209 to obtain a hand-made paper. For comparison, the same procedure was performed on waste paper pulp that was not treated with cellulase to obtain a sample untreated with cellulase. The brightness of the hand-made paper was determined using a reflectance measuring instrument in accordance with JIS P-8123. Measurement was similarly performed for the sample untreated with cellulase and the value obtained by subtracting the brightness of the sample untreated with cellulase from the brightness of the cellulase treated sample was defined as Δ brightness (deinking activity).

When the deinking activity of individual components of cellulase is compared, although superior deinking activity can not be found for cellobiohydrolase, which is considered to promote degradation from the terminus of cellulose, at an added enzyme level in the range of 0.001 to 0.1% (w/w) with respect to oven-dried pulp. However, for endoglucanase, which is considered to randomly degrade the cellulose chain, deinking activity can be found at the low added enzyme level of 0.01% (w/w) or less. Further, when enzymatic treatment is carried out at an excessive level such as 0.1% (w/w), the deinking effect declines.

In the method of waste paper deinking using cellulase, the added level of cellulase is shown by the cellulase activity or the cellulase weight with respect to the weight of normal dry pulp. Regarding the added amount of cellulase, any amount can be added as long as it is within the range of amounts that can exert a deinking effect. However, normally the minimum amount adequate for exhibiting effective deinking activity is added due to cost considerations. When an enzyme dosage that can exert a deinking effect is represented by the pulp-swelling activity (PSA) proposed herein, it can be defined as a cellulase dosage that exhibits activity of 25 U or more with respect to 0.5 g of oven-dried pulp. Further, regarding the level of added cellulase, when representing enzyme activity using hydroxymethyl cellulose (HEC) as a substrate, if an enzyme amount that reduces 1 nmol of substrate with respect to 1 g of oven-dried pulp is defined as 1 nkat/g pulp, a cellulase amount within the range of 0.01 nkat/g pulp to 10000 nkat/g pulp can be added. Preferably, an added level is 100 nkat/g pulp or less, and more preferably 10 nkat/g pulp or less.

In the common deinking processes, after suspending waste paper in water and disintegrating it using a disintegrating apparatus such as a pulper, deinking agents such as sodium hydroxide, sodium silicate, hydrogen peroxide or chelating agents are added thereto and aging is performed. The waste paper is then deinked by subjecting it to flotation or washing it together with a deinking agent that is a surfactant to remove printing ink. Preferably, the cellulase treatment according to the method of waste paper deinking provided by the present invention is employed at the same time as the disintegration step or at the time of aging after the disintegration step instead of the conventionally used deinking agents. At that time, in order to exert cellulase activity at its maximum, the pH can be adjusted using a quantity of acid or alkali, such as sulfuric acid or sodium hydroxide, such that the waste paper pulp is maintained at the optimal pH of the cellulase, and addition of a buffer solution is also possible.

Waste paper subjected to cellulase deinking may be any normally used waste paper, and preferable examples thereof include waste newspaper, magazine waste paper, office waste paper, and the like.

BEST MODE FOR CARRYING OUT THE INVENTION

The present invention will now be described in further detail by means of examples. However, the examples are not intended to limit the scope of the present invention.

EXAMPLE 1

Determination of Pulp-swelling Activity (PSA) of *Trichoderma* Genus-derived Endoglucanase II (EGII) and Cellobiohydrolase I (CBHI)

0.5 g of oven-dried waste newspaper that was disintegrated for 20 min using a standard disintegrator (TAPPI Pulp Disintegrator, manufactured by Toyo Seiki Seisaku-sho, Ltd.) was suspended in a 50 mM citrate buffer solution (pH 5) to bring the pulp consistency to 1% (w/v). Purified EGII or purified CBHI prepared from commercially available Meicelase TP 60 (Meiji Seika Kaisha, Ltd.) based on the method of Rahkamo, L. et al. (Cellulose, 3, 153-163 (1996)) was then added thereto at 0.02% (w/w) with respect to the oven-dried pulp. After reaction at 50° C. for 60 min, the degree of pulp swelling was determined based on the method for measuring the water retention value (WRV) of pulp described on p. 73 of "KAMI PARUPU NO SHIKEN-HOU (A method for testing paper pulp)" (edited and published by The Japan Technical Association of the Pulp and Paper Industry, 1995). Pulp-swelling activity (PSA) was determined by comparing the water retention value of pulp treated with enzyme with the water retention value of untreated pulp, and taking enzyme activity that increased the water retention value by 1% as 10 units (10 U). The results are shown in Table 1. The results in Table 1 show that under the above reaction conditions, although cellobiohydrolase exhibits no pulp-swelling action, endoglucanase exhibits a pulp-swelling action that increases the water retention value of pulp.

TABLE 1

| Enzyme | PSA [U] |
| --- | --- |
| Untreated | — |
| EGII | 35 |
| CBHI | 0 |

EXAMPLE 2

Deinking Test

Twenty-four grams of oven-dried waste newspaper cut into 3 cm-square pieces was disintegrated using a standard disintegrator as described in JIS P-8209 (TAPPI Pulp Disintegrator, manufactured by Toyo Seiki Seisaku-sho, Ltd.) at 50° C. for 20 min. The obtained waste paper pulp was adjusted to pH 5 with a 50 mM citrate buffer solution, and cellulase was then added thereto to bring to respective dosage of 0.001, 0.01, and 0.1% (w/w) with respect to the oven-dried pulp, and enzyme reaction was conducted for 1 hour at 50° C. The cellulases used were CBHI, i.e., cellobiohydrolase, and SCE3 (described in WO 98/54332), in which the endoglucanase component is enhanced, of *Trichoderma* genus, for which the optimal pH is in the vicinity of pH 5; and NCE2 (described in JP Patent Publication (Unexamined Application) No. 8-126492), in which cellobiohydrolase is enhanced, and NCE4 (described in WO 98/03640), in which the endoglucanase component is enhanced, of *Humicola* genus, for which the optimal pH is in the vicinity of pH 6. After reaction, distilled water at 50° C. was added to the waste paper pulp to bring to 4.5 L, the mixture was then provided to an experimental flotator (FW model flotation test apparatus, manufactured by KYOUSIN SANGYOU CO., LTD.), and a deinking agent (Lipotol LH-350, manufactured by NICCA Chemical Co., Ltd.) of 0.3% (w/v) of the oven-dried pulp was added thereto, and flotation was conducted for 10 min. Thereafter, the pulp was recovered using a 140 mesh sieve, washed with distilled water and dehydrated. It was then diluted with distilled water to bring to a pulp consistency of 0.15% (w/v), and a hand-made paper was then prepared using a handsheets machine by the method described in JIS P-8209. For comparison, the same procedure was performed on waste paper pulp that was not treated with cellulase to obtain a sample untreated with cellulase. The brightness of the hand-made paper was determined using a reflectance measuring instrument (spectrophotometer CM5251, manufactured by Minolta) in accordance with JIS P-8123. The difference between the brightness of the cellulase treated sample and the brightness of the sample untreated with cellulase was defined as Δ brightness. Further, the PSA was determined in the same manner as in Example 1. The tensile strength and tear strength were determined in accordance with JIS P-8113 and JIS P-8116, respectively, and the tensile index and tear index were calculated.

Tables 2 and 3 show the results of measurement of the deinking effect of cellobiohydrolase and endoglucanase of *Trichoderma* genus and *Humicola* genus. The results in Table 2 show that no deinking effect was observed for cellobiohydrolase which does not have a swelling action. Further, the results of Table 3 showed that, in the low dosage level of 0.01% (w/w) or less of oven-dried pulp weight in which PSA is 25 U or more, endoglucanase having a pulp swelling action has a deinking effect without causing a significant decrease in intensity. In addition, it was found that when enzymatic treatment is conducted at the excessive level of 0.1% (w/w), the deinking effect is decreased or the intensity declines. Furthermore, when we analyzed the intensity of waste paper treated with endoglucanase of the low dosage of 0.01% (w/w) of oven-dried pulp weight in which PSA is 25 U or more, an action of cellulase that lowers the paper strength that was observed in the conventional cellulase deinking treatment (0.1% treatment in Table 3) was hardly observed, indicating that the negative effect regarding intensity caused by cellulase treatment had been overcome.

TABLE 2

| Enzyme/added level | Brightness | Δ Brightness | PSA [U] |
| --- | --- | --- | --- |
| Untreated (pH 5) | 43.3 | — | — |
| CBHI/0.001% | 43.1 | −0.2 | 0 |

TABLE 2-continued

| Enzyme/added level | Brightness | Δ Brightness | PSA [U] |
|---|---|---|---|
| CBHI/0.01% | 43.2 | −0.1 | 0 |
| CBHI/0.1% | 42.7 | −0.6 | 0 |
| Untreated (pH 6) | 43.5 | — | — |
| NCE2/0.001% | 42.2 | −1.3 | 0 |
| NCE2/0.01% | 43.4 | −0.1 | 0 |
| NCE2/0.1% | 43.5 | 0 | 0 |

TABLE 3

| Enzyme/added level | Brightness | Δ Brightness | PSA [U] | Tensile index [NM/g] | Tear index [mNm2/g] |
|---|---|---|---|---|---|
| Untreated (pH 5) | 43.3 | — | — | 27.5 | 6.4 |
| SCE3/0.001% | 44.0 | 0.7 | 29 | 28.2 | 6.4 |
| SCE3/0.01% | 47.0 | 3.7 | 97 | 26.3 | 6.0 |
| SCE3/0.1% | 45.0 | 1.7 | 19 | 23.8 | 4.2 |
| Untreated (pH 6) | 43.5 | — | — | 27.8 | 6.2 |
| NCE4/0.001% | 46.0 | 2.5 | 32 | 28.2 | 6.2 |
| NCE4/0.01% | 44.7 | 1.2 | 56 | 28.4 | 6.1 |
| NCE4/0.1% | 44.6 | 1.1 | 8 | 25.2 | 5.8 |

EXAMPLE 3

Comparison of Conventional Chemical Deinking and Enzymatic Deinking

We investigated the effect of enzymatic deinking with regard to lowering the usage amount of chemical deinking agents, taking the standard usage amount of conventionally used deinking agents to be 1.5% (w/w) sodium hydroxide+3% (w/w) sodium silicate+0.5% (w/w) hydrogen peroxide with respect to oven-dried pulp. In the same manner as in Example 2, waste paper pulp subjected to enzymatic treatment with SCE3 of 0.01% (w/w) was treated with deinking agents of usage amounts graded in three steps, i.e., the usage amounts were ¼, ½, and the equivalent of the above standard usage amount, respectively. Treatment with the agents was performed by immersing the waste paper pulp in the agents for 60 min at 50° C. Thereafter, the brightness was determined in the same manner as in Example 2. The results are shown in Table 4. The Δ brightness of untreated+agents (section of experiment with no enzymatic treatment and use of the standard amount of deinking agents) and the Δ brightness of SCE3+½ agents (section of experiment with a step of treatment with SCE3 of 0.01% and use of ½ the standard amount of deinking agents) were roughly equal. Thus, it was found that use of cellulase treatment in deinking treatment makes it possible to decrease the usage amount of deinking agents by approximately ½.

TABLE 4

| Treatment condition | Brightness | Δ Brightness |
|---|---|---|
| Untreated | 43.5 | — |
| Untreated + agents | 49.1 | 5.6 |
| SCE3 | 44.7 | 1.2 |
| SCE3 + ¼ agents | 45.0 | 1.5 |
| SCE3 + ½ agents | 48.6 | 5.1 |
| SCE3 + agents | 51.1 | 7.6 |

INDUSTRIAL APPLICABILITY

The present invention enables the evaluation and selection of cellulase having effective pulp swelling activity in waste paper deinking, and provides a low cost method of deinking waste paper that is kind to the environment in which the amount of deinking agents used is reduced without lowering paper strength, using an enzyme dosage that is lower than the dosage used conventionally.

All publications, patents and patent applications cited herein are incorporated herein by reference in their entirety. Also, it will be readily understood by a person skilled in the art that miscellaneous variations and modifications of the present invention are possible without deviating from the technical ideas and scope of the invention as disclosed in the attached claims. The present invention is also intended to encompass such variations and modifications.

The invention claimed is:

1. A deinking method for waste paper without lowering paper strength comprising treating waste paper with endoglucanase, wherein:

(a) the endoglucanase is used at 0.01 % (w/w) or less with respect to oven-dried pulp; and (b) the endoglucanase is used at a dosage exhibiting a pulp-swelling activity (PSA) which is 25 units (25 U) or more.

2. The method of claim 1, in which the endoglucanase is SCE3 derived from *Trichoderma* genus, NCE4 derived from *Humicola* genus, or RCEI derived from *Rhizopus* genus.

* * * * *